(12) United States Patent
Elder et al.

(10) Patent No.: US 9,404,794 B2
(45) Date of Patent: Aug. 2, 2016

(54) AMBIENT LIGHT COMPENSATION CIRCUIT FOR ANALYTE MEASUREMENT SYSTEMS

(71) Applicant: LifeScan Scotland Limited, Inverness, Inverness-shire (GB)

(72) Inventors: David Elder, Inverness (GB); Lawrence Ritchie, Inverness (GB); Paul Knight, Bedfordshire (GB)

(73) Assignee: LifeScan Scotland Limited, Inverness (GB)

( * ) Notice: Subject to any disclaimer, the term of this patent is extended or adjusted under 35 U.S.C. 154(b) by 669 days.

(21) Appl. No.: 13/780,518

(22) Filed: Feb. 28, 2013

(65) Prior Publication Data

US 2014/0238874 A1 Aug. 28, 2014

(51) Int. Cl.
| | |
|---|---|
| *G01J 1/42* | (2006.01) |
| *G01N 33/487* | (2006.01) |
| *G01J 1/02* | (2006.01) |
| *G01J 1/46* | (2006.01) |

(52) U.S. Cl.
CPC .............. *G01J 1/4204* (2013.01); *G01J 1/0219* (2013.01); *G01J 1/0228* (2013.01); *G01J 1/0271* (2013.01); *G01J 1/46* (2013.01); *G01N 33/48785* (2013.01); *G01J 2001/0257* (2013.01)

(58) Field of Classification Search
None
See application file for complete search history.

(56) References Cited

U.S. PATENT DOCUMENTS

| | | |
|---|---|---|
| 5,463,467 A | 10/1995 | Baumann et al. |
| 6,525,330 B2 | 2/2003 | Paolini et al. |
| 6,562,625 B2 | 5/2003 | Modzelewski et al. |
| 6,812,466 B2 | 11/2004 | O'Connor et al. |
| 6,952,263 B2 | 10/2005 | Weiss et al. |
| 7,128,264 B2 | 10/2006 | Barkan et al. |
| 7,758,812 B2 | 7/2010 | Pachl et al. |
| 7,891,570 B2 | 2/2011 | Difazio et al. |
| 8,083,993 B2 | 12/2011 | Groll |
| 2003/0207454 A1 | 11/2003 | Eyster et al. |
| 2006/0110283 A1 | 5/2006 | Fish |
| 2009/0155921 A1 | 6/2009 | Lu et al. |
| 2010/0060562 A1 | 3/2010 | Hadwen et al. |

FOREIGN PATENT DOCUMENTS

DE 197 08 216 A1 2/1997

OTHER PUBLICATIONS

"The Op Amp" from Microcomputers and Electronic Instrumentation: Making the Right Connections, H. V. Malmstadt, et al., 1994, ISBN 0-8412-2861-2, p. 126-127.*
Huang, Tianyu, "DC-blocking/High-Pass Filtered Photodiode Transimpedance Amplifier," posted as http://e2e.ti.com/support/amplifiers/precision_amplifiers/f/47/t/235772.aspx, as printed on Feb. 12, 2013 (2 pgs.).

* cited by examiner

*Primary Examiner* — J. Christopher Ball

(57) ABSTRACT

A blood analyte measurement system is configured to receive a test strip. An LED proximate to the test strip is used to illuminate the test strip and, in conjunction with a photodiode, to determine its type. A compensation circuit of the measurement system insures that ambient light does not cause interference with the LED illumination to prevent saturation of the photodiode.

23 Claims, 4 Drawing Sheets

AMBIENT LIGHT COMPENSATION CIRCUIT FOR ANALYTE MEASUREMENT SYSTEMS

TECHNICAL FIELD

This application generally relates to the field of portable analyte meters and more specifically to blood glucose or cholesterol measurement systems that are configured for performing various functions in a variety of user surroundings.

BACKGROUND

Hand held blood analyte measurement systems are used for testing an individual's blood in a variety of surroundings at any time of day. These systems typically comprise an analyte meter that is configured to receive a biosensor, usually in the form of a test strip. Because these systems are portable, and testing can be completed in a short amount of time, patients are able to use such devices almost anywhere in the normal course of their daily lives without significant interruption to their personal routines. Therefore, a person with diabetes may measure their blood glucose levels several times a day as a part of a self management process to ensure proper control of their blood glucose within a target range. In the course of conducting typical day to day activities, the individual may perform a blood glucose test in a variety of locations under various ambient lighting conditions, such as in an airport, while seated in a darkened movie theater, outside in a park, or dining at a restaurant.

There currently exist a number of available portable electronic devices that can measure analyte levels in an individual based on a small sample of blood. Different test strips perform different analyte measurements and must be automatically identified by the analyte meter when a sample is provided to the meter by a user inserting the test strip into a test strip port. Typically, an LED at the test strip port illuminates the test strip while a photodiode at the test strip port detects properties of the response by the test strip to the LED light in order to identify the type of test strip that has been inserted. Such detection systems operate effectively so long as ambient light does not interfere with the photodiode. In bright daylight, for example, the photodiode may be adversely affected and may drive its associated detection circuitry into saturation, thereby preventing an accurate reading of the test strip type.

SUMMARY OF THE DISCLOSURE

Therefore and according to a first aspect, there is provided an ambient light compensation circuit comprising a first gain stage having a voltage source, a power supply, and a photodiode connected to the voltage source. An operational amplifier is connected to the photodiode and the power supply. A coupling capacitor is connected to an output of the operational amplifier and to a second gain stage. The coupling capacitor transmits a voltage pulse from the first gain stage to the second gain stage.

According to another aspect, there is provided a blood analyte measurement system that includes, but is not limited to, a processing unit, a test strip port for receiving a test strip, and an LED proximate the test strip port for illuminating the test strip. The LED is activated by a signal from the processing unit and a photodiode detects light from the test strip. A compensation circuit is used to detect a level of ambient light impacting the photodiode.

According to another aspect, an automated method of operating a blood analyte measurement system includes receiving a test strip and monitoring a voltage level of a compensation circuit in the analyte meter. The compensation circuit is responsive to ambient light intensity, so the test strip is analyzed only if its voltage level has remained substantially constant for a preselected time duration.

These and other embodiments, features and advantages will become apparent to those skilled in the art when taken with reference to the following more detailed modes of carrying out the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient" or "user" refer to any human or animal subject and are not intended to limit the systems or methods to human use, although use of the subject invention in a human patient represents a preferred embodiment.

Figure 1:
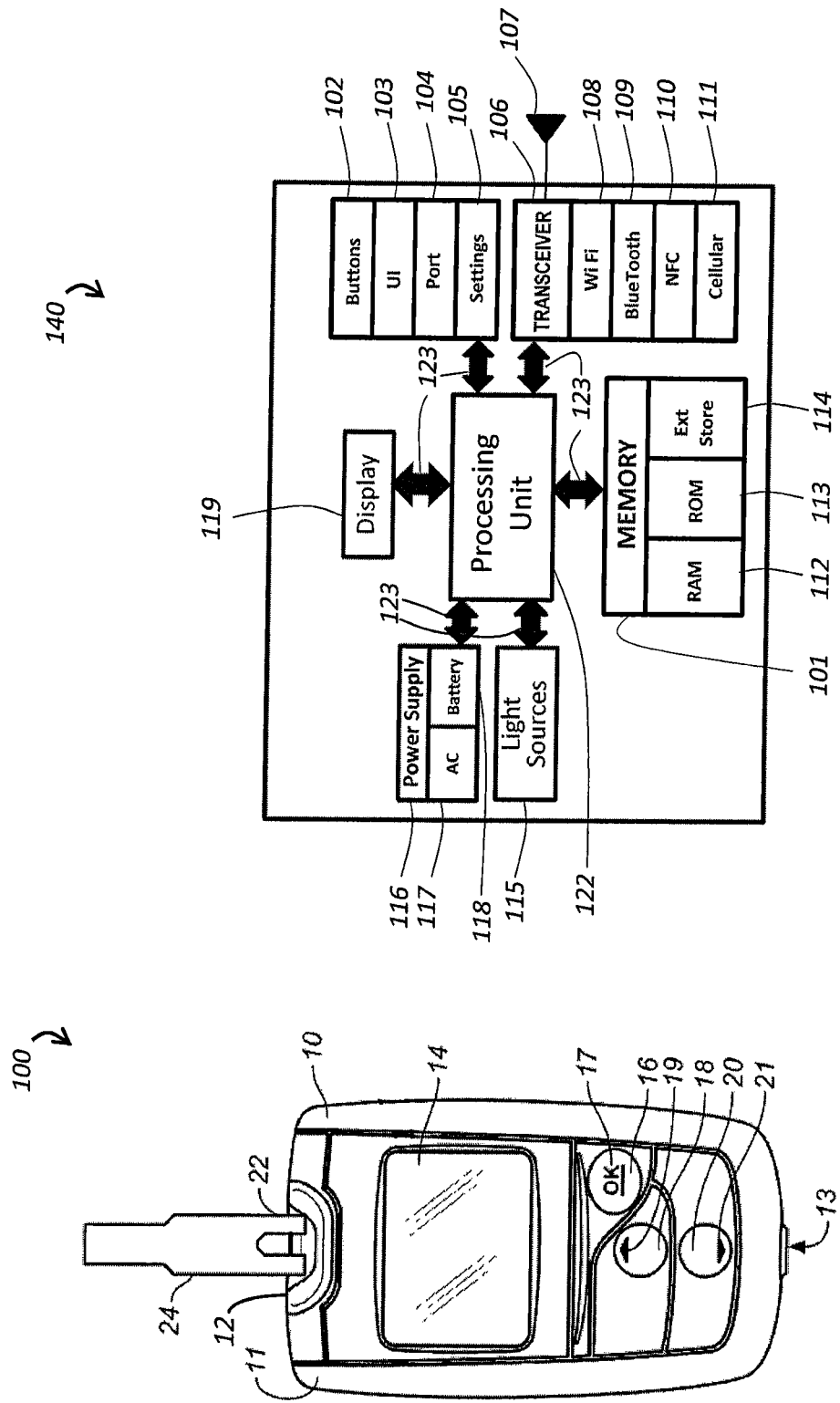
FIG. 1A illustrates a diagram of an exemplary blood analyte measurement system.
FIG. 1B illustrates a diagram of an exemplary processing system of the blood analyte measurement system of FIG. 1A.

FIG. 1A illustrates an analyte measurement system 100 that includes an analyte meter 10. The analyte meter 10 is defined by a housing 11 that retains a processing system 140 and further includes a port 22 sized for receiving a biosensor. In one embodiment, the analyte meter 10 is a blood glucose meter and the biosensor is provided in the form of a glucose test strip 24 for performing blood glucose measurements. The analyte meter 10 includes a processing system 140, FIG. 1B, disposed within the interior of the meter housing 11, a plurality of user interface buttons (16, 18, and 20), a display 14, a strip port connector 22, a strip port illumination panel 12, and a data port 13, as illustrated in FIG. 1A. The plurality of user interface buttons (16, 18, and 20) can be configured to allow the entry of data, to prompt an output of data, to navigate menus presented on the display 14, and to execute commands. Output data can include values representative of analyte concentration presented on the display 14. Input information, which is related to the everyday lifestyle of an individual, can include food intake, medication use, occurrence of health check-ups, and general health condition and exercise levels of an individual. These inputs can be requested via prompts presented on the display 14 and can be stored in a memory module of the analyte meter 10. Specifically and according to this exemplary embodiment, the user interface buttons 16, 18, and 20 include a first user interface button 16, a second user interface button 18, and a third user interface button 20. In that regard, the user interface buttons (16, 18, and 20) further include a first marking 17, a second marking 19, and a third marking 21, respectively, which allow a user to navigate through the user interface presented on the display 14. Although the buttons 16, 18, 20 are shown herein as mechanical switches, a touch screen interface with virtual buttons may also be utilized.

The electronic components of the glucose measurement system 100 can be disposed on, for example, a printed circuit board situated within the housing 11 and forming the processing system 140 of the herein described system. FIG. 1B illustrates, in simplified schematic form, several of the electronic components disposed within the housing 11 for purposes of this embodiment. The processing system 140 includes a processing unit 122 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below. The processing unit 122 is electrically connected to, for example, a test strip port circuit 104 via a communication line 123. The test strip port circuit as described herein includes a novel ambient light compensation circuit as will be described below. The strip port circuit 104 is electrically connected to a strip port connector 22 during, for example, blood glucose testing although other blood analyte levels may also be tested, such as a cholesterol level. To measure analyte concentration, the strip port circuit may first determine the type of test strip that has been inserted into the test strip port, as described below, which then controls, for example, whether a glucose test or a cholesterol test will be performed by the processing system 140.

In a glucose test, for example, the strip port circuit 104 detects a resistance across electrodes of analyte test strip 24 having a blood sample disposed thereon, using a potentiostat, and converts an electric current measurement into digital form for presentation on the display 14. The processing unit 122 can be configured to receive input from the strip port circuit 104 and may also perform a portion of the potentiostat function and the current measurement function. In one embodiment, the analyte test strip 24 can be in the form of an electrochemical glucose test strip. The test strip 24 can include one or more working electrodes. Test strip 24 can also include a plurality of electrical contact pads, where each electrode can be in electrical communication with at least one electrical contact pad. Strip port connector 22 can be configured to electrically interface to the electrical contact pads and form electrical communication with the electrodes. Test strip 24 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then be used to measure a concentration of the reduced mediator in the form of a current. In turn, strip port circuit 104 can convert the current magnitude into, for example, a glucose concentration.

A display module 119, which may include a display processor and display buffer, is electrically connected to the processing unit 122 over the communication line 123 for receiving and displaying output data, and for displaying user interface input options under control of processing unit 122. The structure of the user interface, such as menu options, is stored in user interface module 103 and is accessible by processing unit 122 for presenting menu options to a user of the blood glucose measurement system 100. User interface module 103 receives inputs via user interface buttons 16, 18, and 20 which are processed and transmitted to the processing unit 122 over the communication line 123.

A memory module 101, that includes but are not limited to volatile random access memory ("RAM") 112, a non-volatile memory 113, which may comprise read only memory ("ROM") or flash memory, and a circuit 114 for connecting to an external portable memory device via a data port 13, is electrically connected to the processing unit 122 over a communication line 123. External memory devices may include flash memory devices housed in thumb drives, portable hard disk drives, data cards, or any other form of electronic storage devices. The on-board memory can include various embedded applications executed by the processing unit 122 for operation of the analyte meter 10, as will be explained below. On board memory can also be used to store a history of a user's blood glucose measurements including dates and times associated therewith. Using the wireless transmission capability of the analyte meter 10 or the data port 13, as described below, such measurement data can be transferred via wired or wireless transmission to connected computers or other processing devices.

A wireless module 106 may include transceiver circuits for wireless digital data transmission and reception via one or more internal digital antennas 107, and is electrically connected to the processing unit 122 over communication line 123. The wireless transceiver circuits may be in the form of integrated circuit chips, chipsets, programmable functions operable via processing unit 122, or a combination thereof. Each of the wireless transceiver circuits is compatible with a different wireless transmission standard. For example, a wireless transceiver circuit 108 may be compatible with the Wireless Local Area Network IEEE 802.11 standard known as WiFi. Transceiver circuit 108 is configured to detect a WiFi access point in proximity to the analyte meter 10 and to transmit and receive data from such a detected WiFi access point. A wireless transceiver circuit 109 may be compatible with the Bluetooth protocol and is configured to detect and process data transmitted from a Bluetooth "beacon" in proximity to the analyte meter 10. A wireless transceiver circuit 110 may be compatible with the near field communication ("NFC") standard and is configured to establish radio communication with, for example, an NFC compliant point of sale terminal at a retail merchant in proximity to the analyte meter 10. A wireless transceiver circuit 111 may comprise a circuit for cellular communication with cellular networks and is configured to detect and link to available cellular communication towers.

A power supply module 116 is electrically connected to all modules in the housing 11 and to the processing unit 122 to supply electric power thereto. The power supply module 116 may comprise standard or rechargeable batteries 118 or an AC power supply 117 may be activated when the analyte meter 10 is connected to a source of AC power. The power supply module 116 is also electrically connected to processing unit 122 over the communication line 123 such that processing unit 122 can monitor a power level remaining in a battery power mode of the power supply module 116.

In addition to connecting external storage for use by the analyte meter 10, the data port 13 can be used to accept a suitable connector attached to a connecting lead, thereby allowing the analyte meter 10 to be wired to an external device such as a personal computer. Data port 13 can be any port that allows for transmission of data such as, example, a serial, USB, or a parallel port.

Figure 2:
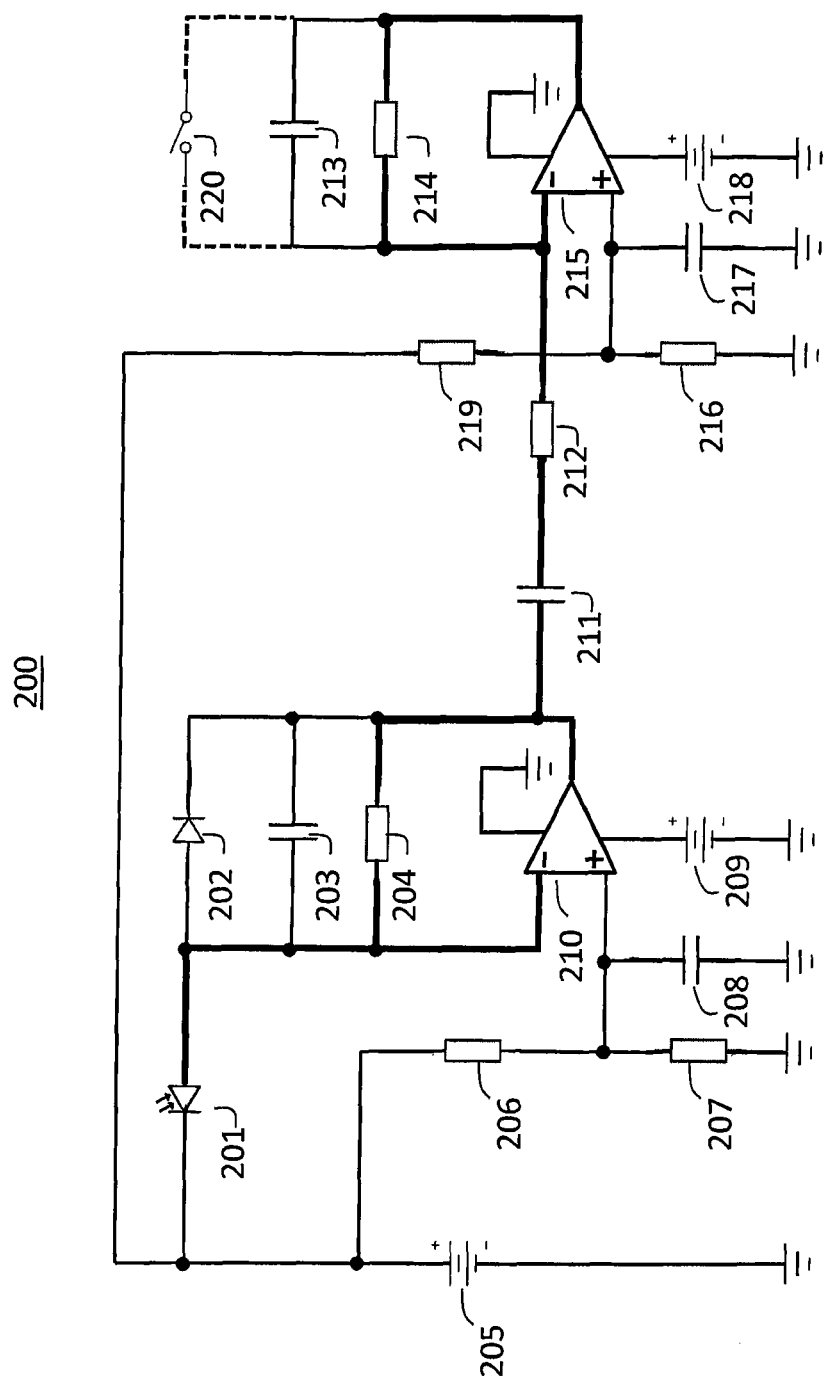
FIG. 2 illustrates a schematic diagram of an exemplary ambient light compensation circuit.

With reference to FIG. 2 an exemplary ambient light compensation circuit is illustrated which comprises a portion of the strip port test circuit 104 and cooperates with the strip port test circuit 104 under control of processing unit 122, as follows. The photodiode 201 is illustrated as a current source which is activated in response to a light pulse generated by an LED (FIG. 3) that bounces off the test strip 24 inserted into the test strip port. The characteristics of this light, as detected by photodiode 201, are analyzed by the processing unit 122 to determine the type of the test strip. A biasing voltage source 205, of approximately two volts, is connected to the photodiode 201 which generates a current therethrough on the order of tens of nanoamps. The output of the photodiode 201 is connected in parallel to the inverting input of the first stage operational amplifier 210, resistor 204, capacitor 203, and diode 202. A voltage signal is generated at the output of the operational amplifier 210 proportional to both the size of resistor 204 and the generated photodiode current traveling therethrough. Diode 202 serves to limit the output voltage of operational amplifier 210, and capacitor 203 stabilizes the circuit by providing a roll off of the first stage operational amplifier output. The output of operational amplifier 210 is also connected in parallel to resistor 204, capacitor 203, and diode 202.

The signal at the output of operational amplifier 210 then travels to a second gain stage via coupling capacitor 211 and resistor 212, and to the inverting input of second stage operational amplifier 215, and generates a voltage signal at the output of second stage operational amplifier 215 proportional to both the size of resistor 214 and the current traveling therethrough. Capacitor 211 and resistor 212 are selected to provide a time constant larger than the LED pulse width to avoid distortion of the pulse signal. Resistor 214 and capacitor 213 are connected in parallel to the inverting input of operational amplifier 215 and its output. Capacitor 213 stabilizes the second stage by providing a roll off of the second stage operational amplifier output. The output of the operational amplifier 215 is transmitted to the analyte meter 100 for determining a type of the test strip. The analyte meter detects an amplitude and a decay time of the received signal to determine the test strip type. Preselected compounds may be deposited on the test strip in order to regulate these characteristics of the received signal, thereby providing a means whereby the processing system 140 of the analyte meter 100 may detect and classify test strips according to their type, using the circuit described herein.

With reference to the first gain stage of the circuit of FIG. 2, resistors 206 and 207 are connected in parallel to non-inverting input of operational amplifier 210 and between the bias voltage source 205 and ground in series. The resistors are selected so as to provide a non-inverting reference input to operational amplifier 210 of about 1.3V, thereby reverse biasing photodiode 201 at about −0.7V. Capacitor 208 is connected to the non-inverting input of operational amplifier 210 and to ground for noise decoupling. Power supply voltage 209 is a 3V supply and is connected to operational amplifier 210 power supply input while the negative power supply terminal is grounded. With reference to the second gain stage of the circuit of FIG. 1, resistors 216 and 219 are connected in parallel to non-inverting input of operational amplifier 215 and between bias voltage source 205 and ground in series, and are selected so as to provide a non-inverting reference input to operational amplifier 215 of about 0.5V. Resistors 212 and 214 are connected in parallel to the inverting input of operational amplifier 215, and are selected so as to provide a second stage gain of about 200. Capacitor 217 is connected to the non-inverting input of operational amplifier 215 and to ground for noise decoupling. Power supply voltage 218 is a 3V supply to operational amplifier 215 while the negative supply terminal is grounded. Suitable operational amplifiers include the Model LMV791 for the first stage and the Model OPA376 for the second stage, both manufactured by Texas Instruments, of Dallas, Tex., USA.

The operation of the compensation circuit of FIG. 2 just described illustrates the AC coupling provided by capacitor 211 between the first and second gain stages of the circuit 200 for passing the signal generated by the LED pulse bouncing off the test strip 24 as detected by photodiode 201. As illustrated in bold lines in FIG. 2, the AC signal path from photodiode 201 is shown to travel through resistor 204 and to inverting input of operational amplifier 210, which voltage signal at the output of operational amplifier 210 then passes through capacitor 211 and resistor 212 to the inverting input of operational amplifier 215 and resistor 214. The output at operational amplifier 215 is transmitted to the processing system 140.

Thus, the capacitor 211 serves as an AC coupler between the gain stages and, as will now be described, also serves as a blocking capacitor for any DC component generated by ambient light impinging on the photodiode. Ambient light that is present in the vicinity of the analyte meter 100 may impinge upon the photodiode and affect its response to the LED pulse, thereby rendering erroneous any resulting test strip identification procedure, or the ambient light may be bright enough to render the LED pulse undetectable, absent the compensation circuit described herein.

The second gain stage is designed to compensate for charge accumulating on capacitor 211 as a result of ambient light impacting photodiode 201. This DC voltage variation at capacitor 211 is compensated by the output of the second operational amplifier 215 through resistors 212 and 214, as follows. The biasing of the first stage, described above, causes the DC output from the first stage to drop as ambient light increases in intensity, for example, from 1.3V to 0V, resulting in an output of the second stage operational amplifier being driven low and compensating (charging) capacitor 211 by 1.3V. If ambient light then decreases in intensity the output at operational amplifier 210 drives, for example, from 0V to 1.3 V, resulting in an output of the second stage operational amplifier being driven high and compensating (discharging) capacitor 211 by 1.3V. Thus, the size of blocking capacitor 211 determines the compensation delay time and the smaller the size of capacitor 211 the faster the compensation. For minimum distortion of the pulse signal, however, the size of capacitor 211 should be large. Thus, in light of this tradeoff, the size of capacitor 211 may be selected as necessary for particular applications. An alternative circuit configuration includes electronic switch 211, depicted as dashed line in FIG. 2, which may be connected in parallel with capacitor 213 and resistor 214, and controllable (open/close) by processing unit 122 to provide a direct charging path to capacitor 211, thereby reducing the charging time of capacitor 211 almost to a negligible amount, on the order of tens of milliseconds.

Figure 3:
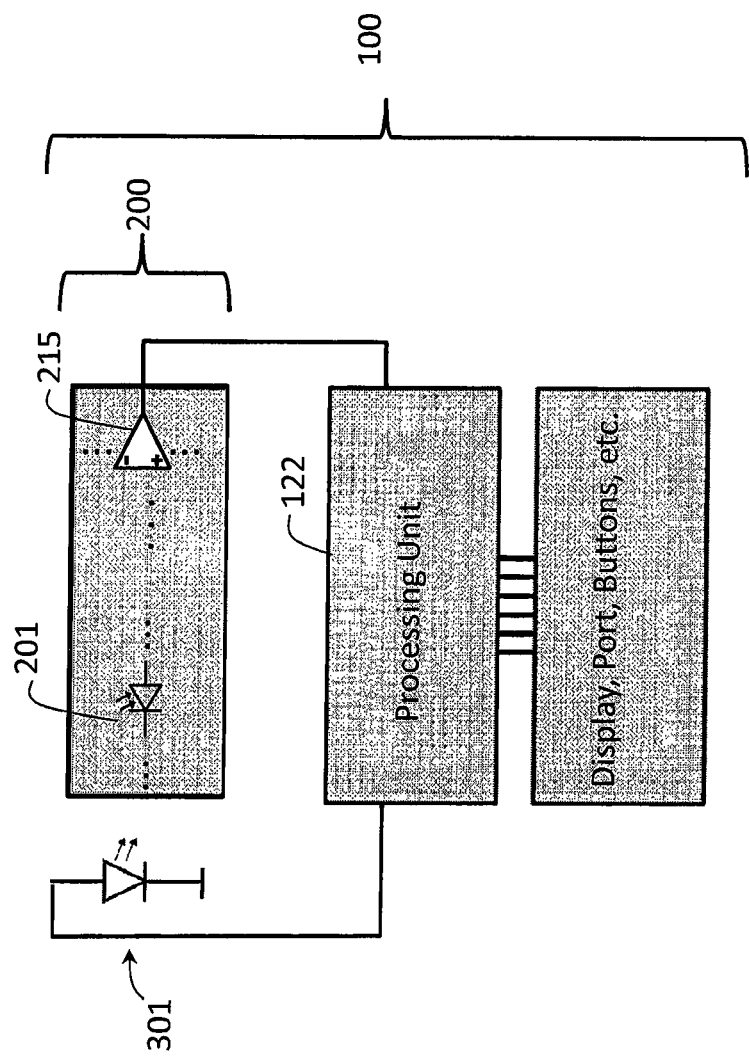
FIG. 3 illustrates an analyte meter having the ambient light compensation circuit of FIG. 1 electrically connected thereto.

With reference to FIG. 3, there is illustrated in simplified form the analyte meter 100 as described above including the ambient light compensation circuit 200, also shown in simplified form. When the analyte meter 100 is powered on, the processing unit 122 monitors an output of operational amplifier 215 to ensure that the ambient light conditions surrounding the analyte meter 100 are not currently in variance such that the output is varying in order to compensate capacitor 211. When the output is detected by processing unit as being in a suitable steady state, i.e., a non-varying ambient light, the processing unit 122 transmits an electric signal of known amplitude and pulse width to LED 301. The LED 301, positioned proximate to an inserted test strip 24, emits a light pulse in response to the electric signal thereby illuminating the test strip and, as described in detail above, the light from the LED 301 reflected from the test strip activates the photodiode 201 which generates a current, via a connected voltage source, that is converted to a voltage signal by the first stage amplifier circuit.

If the alternative electronic switch 220 is implemented in the ambient light compensation circuit 200, the processing unit may be programmed to operate as follows. After the analyte meter is powered on and a test strip having a sample thereon is inserted into the test strip port of the analyte meter, the processing unit, under program control, closes switch 220 to insure charging of capacitor 211, then the processing unit opens the switch and checks for a steady state output before proceeding with the reading, as described above. Additional alternative safety measures may be implemented in software, such as checking and recording the steady state voltage level of the compensation circuit output just prior to a reading and comparing the voltage level at the output just after the reading and measurement of the sample to insure that it has remained substantially the same. If not, it may indicate that a shift in ambient light has occurred during the reading and measurement, which may require that the reading be repeated.

Figure 4:
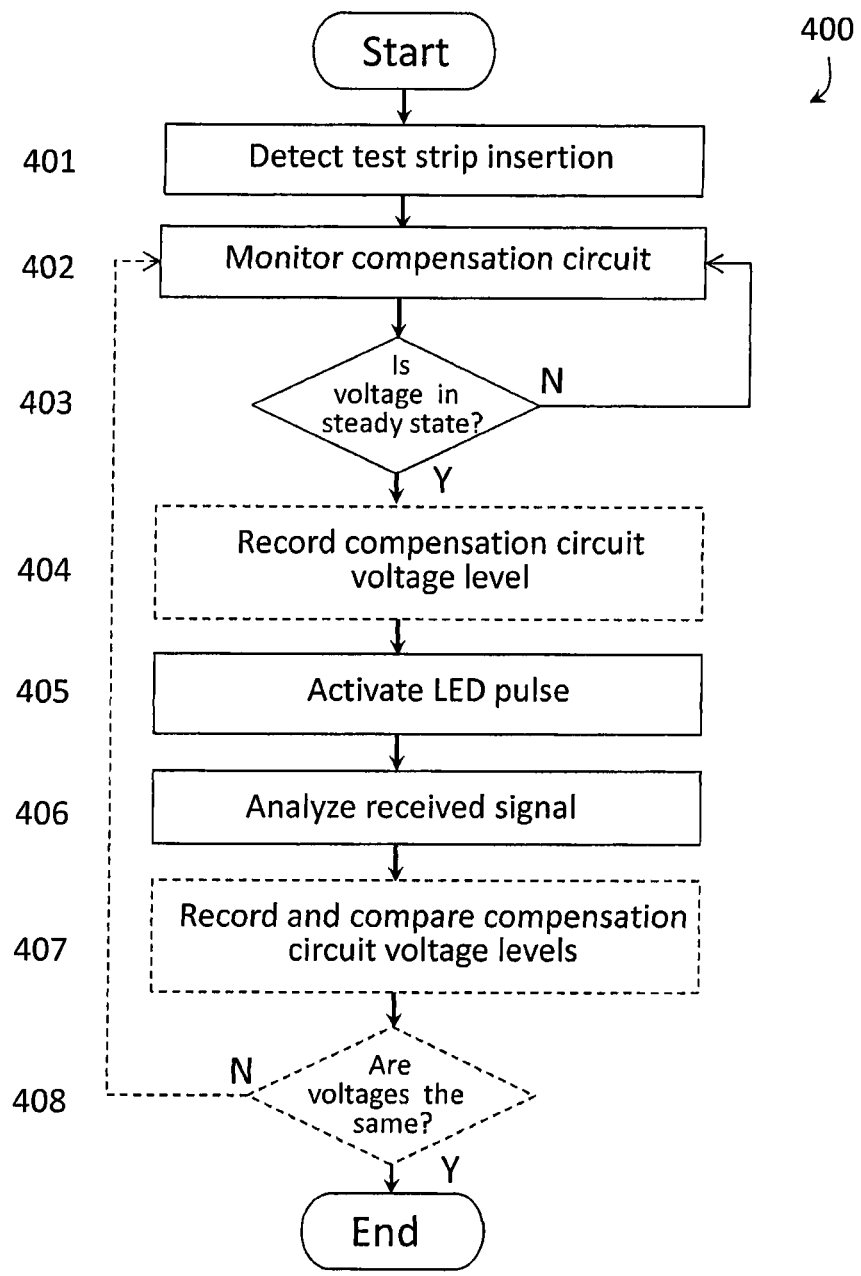
FIG. 4 illustrates a flow chart depicting a method of operating an analyte meter having the compensation circuit of FIG. 2.

With reference to FIG. 4, there is illustrated an algorithm and method of operating an analyte meter having the ambient light compensation circuit as described herein. In a first step, step 401, the analyte meter processing unit receives a signal from the test strip port indicating an insertion of the test strip and in response, at step 402, begins to monitor the compensation circuit output voltage to determine whether the test strip reading may begin. At step 403, if the processing unit determines that the compensation circuit output is not in steady state it will continue to monitor the circuit until its voltage remains substantially unchanged for a preselected programmed time period. At the point in time when the compensation circuit's output voltage maintains a steady state voltage for the preselected programmed time period, the processing unit activates the LED to cause a pulse of light to be emitted therefrom toward a surface of the inserted test strip, at step 405. An alternative step may be included, shown as step 404 and indicated as optional by use of the dashed line box, wherein the measured steady state voltage level is recorded in a memory of the analyte meter processing system. As described above, the LED light pulse aimed at the test strip causes the photodiode portion of the compensation circuit to generate a current pulse which is converted to a voltage signal by the first gain stage amplifier, which is eventually transmitted to the processing system for determining the test strip type, at step 406. If the alternative step 404 is not implemented in this processing system algorithm, the test strip determination procedure is complete. If the alternative step 404 is performed then, in conjunction therewith, the alternative step 407 is performed to measure and record the compensation circuit output voltage after receiving the voltage signal generated by the light pulse, and comparing it with the recorded steady state output voltage level measured previously. If both of the recorded output voltage levels are substantially the same, as determined at step 408, it indicates that ambient light levels did not vary during the time period between readings, and the algorithm is completed. If, at step 408, the recorded output voltages are determined not to be substantially the same it indicates that the ambient light levels have varied and may have altered a level of current generated by the photodiode portion of the compensation circuit. Such an altered current level changes a level of the voltage signal transmitted by the first gain stage and eventually received and processed by the processing system, which may lead to an erroneous result. Thus, the algorithm returns to step 402 and the process of monitoring the compensation circuit voltage level begins again.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Furthermore, the various methods described herein can be used to generate software codes using off-the-shelf software development tools such as, for example, Visual Studio 6.0, C or C++ (and its variants), Windows 2000 Server, and SQL Server 2000. The methods, however, may be transformed into other software languages depending on the requirements and the availability of new software languages for coding the methods.

PARTS LIST FOR FIGS. 1A-4

10 analyte meter
11 housing, meter
12 strip port illumination panel
13 data port
14 display
16 user interface button
17 first marking
18 user interface button
19 second marking
20 user interface button
21 third marking
22 strip port connector
24 glucose test strip
100 blood glucose measurement system
101 memory module
102 buttons module
103 user interface module
104 strip port module
105 DMU settings module
106 transceiver module
107 antenna
108 WiFi module
109 Bluetooth module
110 NFC module
111 GSM module
112 RAM module
113 ROM module
114 external storage
115 light source module
116 power supply module
117 AC power supply
118 battery power supply
119 display module
122 processing unit
123 communication line
140 processing system
200 ambient light compensation circuit
201 photodiode
202 diode
203 capacitor
204 resistor
205 voltage source
206 resistor
207 resistor
208 capacitor
209 voltage source
210 op amp
211 capacitor
212 resistor
213 capacitor
214 resistor
215 op amp
216 resistor
217 capacitor
218 voltage source
219 resistor
220 switch
301 LED
400 method of operating an analyte meter
401 step—detect test strip insertion
402 step—monitor compensation circuit
403 decision step—is voltage in steady state
404 step—record compensation circuit voltage level
405 step—activate LED pulse
406 step—analyze received signal
407 step—record and compare compensation circuit voltage levels
408 decision step—are voltages the same While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An ambient light compensation circuit comprising:
    a first gain stage comprising:
        a voltage source;
        a power supply;
        a photodiode connected to the voltage source;
        a first operational amplifier connected to the photodiode and to the power supply, the first operational amplifier having a first gain stage output terminal;
        a first voltage divider connected to the voltage source and the first operational amplifier for providing a first reference voltage to the first operational amplifier, the voltage divider comprising a first pair of resistors; and
    a coupling capacitor coupled in series to the first gain stage output terminal and to a second gain stage, the coupling capacitor for transmitting a voltage pulse from the first gain stage output terminal to the second gain stage,
    wherein the second gain stage comprises:
        a second operational amplifier connected to the coupling capacitor through a coupling resistor and to the power supply, the second operational amplifier having a compensation circuit output terminal;
        a second voltage divider connected to the voltage source and to the second operational amplifier for providing a second reference voltage to the second operational amplifier, the second voltage divider comprising a second pair of resistors; and
    wherein the compensation circuit output terminal is connected to the coupling resistor through a second stage gain control resistor for compensating a DC voltage of the coupling capacitor, the DC voltage generated by ambient light impacting the photodiode.

2. The ambient light compensation circuit of claim 1, wherein the first gain stage further comprises a first roll off capacitor and a first stage gain control resistor both connected to the first gain stage output terminal and to the photodiode, and a grounded decoupling capacitor connected to the first operational amplifier.

3. The ambient light compensation circuit of claim 1, wherein the first gain stage further comprises a limiter diode connected to the first gain stage output terminal and to the photodiode.

4. The ambient light compensation circuit of claim 1, wherein the voltage pulse from the first gain stage output terminal is generated by a light pulse impacting the photodiode.

5. The ambient light compensation circuit of claim 4, wherein the second gain stage further comprises a roll off capacitor connected to the compensation circuit output terminal and to the coupling resistor, and a grounded decoupling capacitor connected to the second operational amplifier.

6. The ambient light compensation circuit of claim 1, wherein the second gains stage further comprises an electronic switch connected to the compensation circuit output terminal and to the coupling resistor for selectively bypassing the second stage gain control resistor to compensate the DC voltage of the coupling capacitor.

7. An analyte meter comprising:
a processing unit
a test strip port for receiving a test strip inserted therein;
an LED proximate to the test strip port for illuminating the test strip with a light pulse when the LED is activated, the LED electrically connected to the processing unit for receiving an activation signal therefrom;
a photodiode for detecting light from the test strip;
a compensation circuit connected to the photodiode and the processing unit, and configured to detect a level of ambient light impacting the photodiode, and
a circuit for detecting that the test strip is inserted in the test strip port, and wherein the processing unit is programmed to transmit the activation signal to the LED only after the test strip is inserted in the test strip port and that the compensation circuit is in a steady state.

8. The analyte meter of claim 7, wherein the compensation circuit comprises a capacitor configured to accumulate charge generated by the ambient light impacting the photodiode.

9. The analyte meter of claim 8, wherein the compensation circuit comprises:
an amplifier having an input connected to the capacitor and configured for detecting the accumulated charge; and
a compensation output connected to the capacitor and to the processing unit, the amplifier further configured to compensate the accumulated charge on the capacitor through the compensation output.

10. The analyte meter of claim 9, further comprising a circuit for detecting a voltage level of the compensation output, wherein the processing unit detects the steady state by detecting that the voltage level of the compensation output remains substantially steady for a predetermined period of time.

11. The analyte meter of claim 10, wherein the photodiode is configured to generate an electric current upon detecting the light from the test strip, the light from the test strip generated in response to the LED illuminating the test strip with the light pulse.

12. The analyte meter of claim 11, wherein the compensation circuit is configured to generate a voltage signal in response to the electric current, the voltage signal passing through the capacitor and through the compensation output to the processing unit.

13. The analyte meter of claim 12, wherein the processing unit is programmed to determine a type of the test strip in response to the voltage signal.

14. A method of operating an analyte meter, the method comprising:
receiving a test strip;
monitoring a voltage level of a compensation circuit that is responsive to an ambient light intensity proximate to the analyte meter; and
analyzing the received test strip only if the voltage level has remained substantially constant for a preselected time duration.

15. The method of claim 14, further comprising disposing a photodiode in the compensation circuit that is sensitive to the ambient light intensity.

16. The method of claim 15, wherein the step of analyzing comprises emitting a light pulse at the test strip.

17. The method of claim 16, further comprising disposing the photodiode in the compensation circuit such that it is sensitive to the light pulse impacting the test strip.

18. The method of claim 17, further comprising configuring the photodiode to generate a current proportional to the combined ambient light intensity and the light pulse impacting the test strip.

19. The method of claim 18, further comprising configuring the compensation circuit to convert the current to a voltage signal having an amplitude proportional to an amplitude of the current.

20. The method of claim 18, further comprising configuring the compensation circuit to block a portion of the voltage signal corresponding to the ambient light intensity.

21. The method of claim 19, further comprising configuring the compensation circuit to pass a portion of the voltage signal corresponding to the light pulse.

22. The method of claim 20, wherein said configuring the compensation circuit to block a portion of the voltage signal and said configuring the compensation circuit to pass a portion of the voltage signal both comprise disposing a capacitor in the compensation circuit and configuring the compensation circuit to compensate charge accumulating in the capacitor from the blocked portion of the voltage signal.

23. The method of claim 21, further comprising transmitting the portion of the voltage signal corresponding to the light pulse to a processing system for determining a type of the test strip.

* * * * *